(12) United States Patent
Jeong

(10) Patent No.: US 11,998,168 B2
(45) Date of Patent: Jun. 4, 2024

(54) UTERINE CERVICAL IMAGE ACQUISITION APPARATUS

(71) Applicant: AIDOT INC., Seoul (KR)

(72) Inventor: Jae Hoon Jeong, Seongnam-si (KR)

(73) Assignee: AIDOT INC., Seoul (KR)

( * ) Notice: Subject to any disclaimer, the term of this patent is extended or adjusted under 35 U.S.C. 154(b) by 149 days.

(21) Appl. No.: 17/770,246

(22) PCT Filed: Oct. 28, 2020

(86) PCT No.: PCT/KR2020/014755
§ 371 (c)(1),
(2) Date: Apr. 19, 2022

(87) PCT Pub. No.: WO2021/085987
PCT Pub. Date: May 6, 2021

(65) Prior Publication Data
US 2022/0377227 A1 Nov. 24, 2022

(30) Foreign Application Priority Data
Oct. 28, 2019 (KR) .......................... 10-2019-0134613

(51) Int. Cl.
*A61B 1/00* (2006.01)
*H04N 5/72* (2006.01)
*H04N 23/74* (2023.01)

(52) U.S. Cl.
CPC ........... *A61B 1/00042* (2022.02); *H04N 5/72* (2013.01); *H04N 23/74* (2023.01)

(58) Field of Classification Search
CPC .............. A61B 1/00042; A61B 5/4331; A61B 2560/0456; A61B 1/00016; A61B 1/0002;
(Continued)

(56) References Cited

U.S. PATENT DOCUMENTS 9,473,606 B1 * 10/2016 Sumida ............. H04M 1/72409
10,459,627 B2 10/2019 Jun et al. ............. A61B 8/4654
(Continued)

FOREIGN PATENT DOCUMENTS

CN 105030187 A 11/2015
JP 2014-508021 A 4/2014
(Continued)

OTHER PUBLICATIONS

International Search Report dated Feb. 25, 2021, issued to the corresponding International Application No. PCT/KR2020/014755.
(Continued)

*Primary Examiner* — Michael E Teitelbaum
(74) *Attorney, Agent, or Firm* — Stein IP, LLC

(57) ABSTRACT

The present invention relates to a uterine cervical image acquisition apparatus which acquires and displays images of a uterine cervix, and in some cases can automatically diagnose the onset of a disease related to the uterine cervix, the apparatus being characterized by comprising: a main body in which a camera for acquiring uterine cervical images is installed on one side, a user interface for displaying the uterine cervical images and inputting user touch commands is installed on the opposite side, and a handlebar unit is formed in a downward direction; a light source unit which emits light toward the front of the main body; a battery which is positioned inside the handlebar unit to supply power for charging and operation; an operation button unit which includes at least an image capturing button, a zoom-in button, and a zoom-out button formed on the handlebar unit; a memory for storing the captured uterine cervical images; a communication unit for transmitting the uterine cervical images to a reading computer; an image transmission control unit for controlling to store the captured uterine cervical images in the memory, encrypt selected
(Continued)

uterine cervical images, and transmit the encrypted images to the reading computer; a display screen control unit which controls to display, on the left and right or above and below the captured uterine cervical display images, a menu bar for receiving the user touch commands; and a camera control unit which controls zooming and auto-focusing of the camera and the brightness of the light source unit according to operations of the provided button.

24 Claims, 9 Drawing Sheets

(58) Field of Classification Search
CPC .............. A61B 1/00034; A61B 1/0005; A61B 1/00052; A61B 1/303; A61B 1/00011; A61B 1/00039; A61B 1/00045; A61B 1/045; A61B 1/05; A61B 1/06; A61B 1/0661; A61B 5/7271; A61B 1/00186; H04N 5/72; H04N 23/74; G06N 20/00
See application file for complete search history.

(56) References Cited

U.S. PATENT DOCUMENTS

| | | | | |
|---|---|---|---|---|
| 2008/0226148 | A1 | 9/2008 | Gu et al. ...................... 382/128 |
| 2010/0067706 | A1* | 3/2010 | Anan ...................... G09C 5/00 380/28 |
| 2014/0005477 | A1 | 1/2014 | Gupta et al. .................. 600/109 |
| 2014/0135648 | A1 | 5/2014 | Holoien et al. ............... 600/562 |
| 2015/0150440 | A1 | 6/2015 | Salvati et al. |
| 2016/0058362 | A1 | 3/2016 | Wang et al. ......... A61B 5/4331 |
| 2016/0334694 | A1* | 11/2016 | Liu .................... A61B 1/00045 |
| 2018/0116581 | A1 | 5/2018 | Prasad ............... A61B 5/43331 |

FOREIGN PATENT DOCUMENTS

| | | |
|---|---|---|
| KR | 10-2001-0069660 A | 7/2001 |
| KR | 10-2011-0108905 A | 10/2011 |
| KR | 10-2015-0142289 A | 12/2015 |
| KR | 10-2016-0138787 A | 12/2016 |
| KR | 10-2017-0042900 A | 4/2017 |
| KR | 10-2018-0029069 A | 3/2018 |
| KR | 10-2019-0087681 A | 7/2019 |
| WO | WO 2012/060932 A2 | 5/2012 |
| WO | WO 2019/145951 A1 | 8/2019 |
| WO | WO 2019/194945 A1 | 10/2019 |

OTHER PUBLICATIONS

First Examination Report dated Sep. 8, 2022, issued to Indian Application No. 202217027652.
Office Action dated Oct. 11, 2022, issued to Russian Application No. 2022114299.
Japanese Office Action mailed May 17, 2023, issued to Japanese Application No. 2022-525120.

* cited by examiner

Picture album

Green filter

Wireless transfer

Convenient setting

UTERINE CERVICAL IMAGE ACQUISITION APPARATUS

CROSS-REFERENCE TO RELATED APPLICATIONS

This application is a national stage of International Application No. PCT/KR2020/014755, filed Oct. 28, 2020, which claims the benefit of Korean Application No. 10-2019-0134613, filed Oct. 28, 2019, in the Korean Intellectual Property Office, the disclosures of which are incorporated herein by reference.

TECHNICAL FIELD

The present invention relates to an image diagnostic apparatus for diagnosing uterine cervical cancer, and more particularly, to a uterine cervical image acquisition apparatus capable of acquiring and displaying an image of a uterine cervix and, in some cases, automatically diagnosing the onset of a disease related to the uterine cervix.

BACKGROUND ART

Although uterine cervical cancer, along with mammary cancer, is one of two popular female cancer, it is known that the uterine cervical cancer is the easiest cancer to be prevented through early screening, and thus even healthy women need regular checkups once a year.

As the uterine cervical cancer examination techniques, cytology and colposcopy are focused on, but such examination techniques are dependent on reading doctors and have a disadvantage in that it takes a considerable amount of time to obtain result reports.

In order to solve the above problems, technologically advanced countries including China are recently spurring research on automatic image diagnosis technology using artificial intelligence. Therefore, the development and discovery of artificial intelligence engine technology related to medical imaging is also urgently required at the national level, and it is also necessary to develop an image acquisition apparatus that should be preceded in realizing the automatic image diagnosis technology.

Accordingly, the applicant of the present invention has developed a uterine cervical image acquisition apparatus that should be preceded in diagnosing diseases related to a uterine cervix, and furthermore, affiliate programs have also been developed to automatically diagnose uterine cervical cancer-related diseases by interworking with the uterine cervical image acquisition apparatus.

DOCUMENT OF RELATED ART

Patent Document (Patent Document 1) Korean Laid-open Patent Publication No. 10-2011-0108905
(Patent Document 2) Korean Laid-open Patent Publication No. 2001-0069660

SUMMARY OF INVENTION

Technical Problem

The present invention is invented by the above-described necessity, and is directed to providing a uterine cervical image acquisition apparatus that is convenient to install, use, and operate.

Furthermore, the present invention is also directed to providing a uterine cervical image acquisition apparatus which provides a convenience of operation by displaying menu bars on a display unit and improves a convenience of using the apparatus by allowing display positions of menu bars to be manually or automatically changed in consideration of left and right handles of a user of the apparatus.

Further, the present invention is also directed to providing a uterine cervical image acquisition apparatus capable of automatically correcting the inclination of a captured uterine cervical image according to the inclination of a main body of the uterine cervical image acquisition apparatus.

Furthermore, the present invention is also directed to providing a uterine cervical image acquisition apparatus capable of interworking with an application program for a reading doctor, which automatically diagnoses the onset of uterine cervical cancer by automatically reading the uterine cervical image transmitted from each of the above-described uterine cervical image acquisition apparatuses.

Further, the present invention is also directed to providing a uterine cervical image acquisition apparatus that is portable, chargeable, and mountable and allows adjustment of illumination, adjustment of zoom in/out, and adjustment of an angle of an image display surface to be controlled.

Solution to Problem

According to an aspect of the present invention, there is provided a uterine cervical image acquisition apparatus including a main body in which a camera for acquiring a uterine cervical image is installed on one side thereof, a user interface for displaying the uterine cervical image and inputting a user touch command is installed on a side opposite to the one side, and a handlebar unit is formed in a downward direction, a light source unit that irradiates a front of the main body with light, a battery which is positioned in the handlebar unit to supply power for charging and operation, and an operation button unit which at least includes an image capturing button, a zoom-in button, and a zoom-out button formed on the handlebar unit, wherein the uterine cervical image acquisition apparatus includes a memory configured to store the captured uterine cervical image; a communication unit configured to transmit the uterine cervical image to a computer of a reading doctor; an image transmission control unit configured to perform control to store the captured uterine cervical image in the memory, encrypt the selected uterine cervical image, and transmit the encrypted uterine cervical image to the computer of the reading doctor; a display screen control unit configured to perform control to display the captured uterine cervical image and menu bars for receiving the user touch command on left and right or upper and lower sides of the captured uterine cervical image; and a camera control unit configured to control zooming and auto-focusing of the camera and brightness of the light source unit according to operations of the provided button.

Furthermore, in the uterine cervical image acquisition apparatus having the above-described components, the display screen control unit may change display positions of the menu bars in opposite directions and display the menu bars whenever a left and right hand mode setting button displayed on the menu bar is operated.

As another modified embodiment, the uterine cervical image acquisition apparatus having the above-described components may further include a hand detection sensor formed on the handlebar unit to detect a left hand or right hand holding the handlebar unit. In this case, the display screen control unit may change and display the display positions of the menu bars in opposite directions according to an output signal of the hand detection sensor.

Further, the above-described uterine cervical image acquisition apparatus may further include an inclination sensor for detecting a degree of inclination of the main body, and the display screen control unit may correct the inclination of the captured uterine cervical image according to the inclination detected by the inclination sensor.

Advantageous Effects of Invention

According to the above-described solutions, in the uterine cervical image acquisition apparatus according to an embodiment of the present invention, it is possible to capture a uterine cervical image using a camera and wirelessly transmit the captured image to a designated computer of a reading doctor according to a command of the user of the apparatus, and thus the inconvenience of connection of the uterine cervical image acquisition apparatus and the computer of the reading doctor using a cable can be eliminated.

Furthermore, an upper portion of a user interface installed on the rear of the uterine cervical image acquisition apparatus is inclined in a forward direction, and thus, in photographing a uterine cervix of a patient to be treated who lying down, the user of the apparatus can have a convenience of being able to photograph the uterine cervix while viewing the photographing screen conveniently without bending any part of her body such as a knee or head.

Further, a camera image is displayed on the user interface of the uterine cervical image acquisition apparatus according to an embodiment of the present invention and menu bars, in which a plurality of function buttons for apparatus operation and settings are displayed, are all displayed on left and right or upper and lower sides of a region in which the camera image is displayed, and thus there is an advantage in that it can be conveniently operated by holding the handlebar unit with one hand and inputting a touch input on the function buttons provided on the menu bars with the other hand.

Further, in the uterine cervical image acquisition apparatus according to an embodiment of the present invention, main function buttons that are frequently used are positioned to be focused on one of the menu bars, and the position of the menu bar is manually or automatically changed and displayed for a left-handed person or a right-handed person, and thus an effect of providing convenience in operating the apparatus can be obtained. When the uterine cervical image acquisition apparatus is a uterine cervical image acquisition apparatus capable of correcting the inclination of the captured display image by detecting the inclination of the main body, there is an advantage in that a uterine cervical image positioned at a correct position can be acquired even when the uterine cervix is photographed in a state in which the main body is inclined.

Furthermore, in the present invention, there is a convenience of being able to conveniently set the information on an Internet protocol (IP) address and port number of the computer of the reading doctor by just scanning a quick response (QR) code displayed under the support of the application program installed on the computer of the reading doctor.

DETAILED DESCRIPTION OF EMBODIMENT

Specific structural and functional descriptions of embodiments of the present invention disclosed in this specification are only for the purpose of describing embodiments of the present invention, and the embodiments of the present invention may be embodied in various forms and are not to be construed as limited to the embodiments described in this specification.

While the embodiments of the present invention may be modified in various ways and take on various alternative forms, specific embodiments thereof are shown in the accompanying drawings and described in detail in this specification. There is no intent to limit the present invention to the particular forms disclosed. On the contrary, the present invention is to cover all modifications, equivalents, and alternatives falling within the spirit and scope of the appended claims.

In addition, in the description of the present invention, when it is determined that detailed descriptions of related well-known configurations or functions unnecessarily obscure the gist of the present invention, the detailed descriptions will be omitted.

Figure 1:
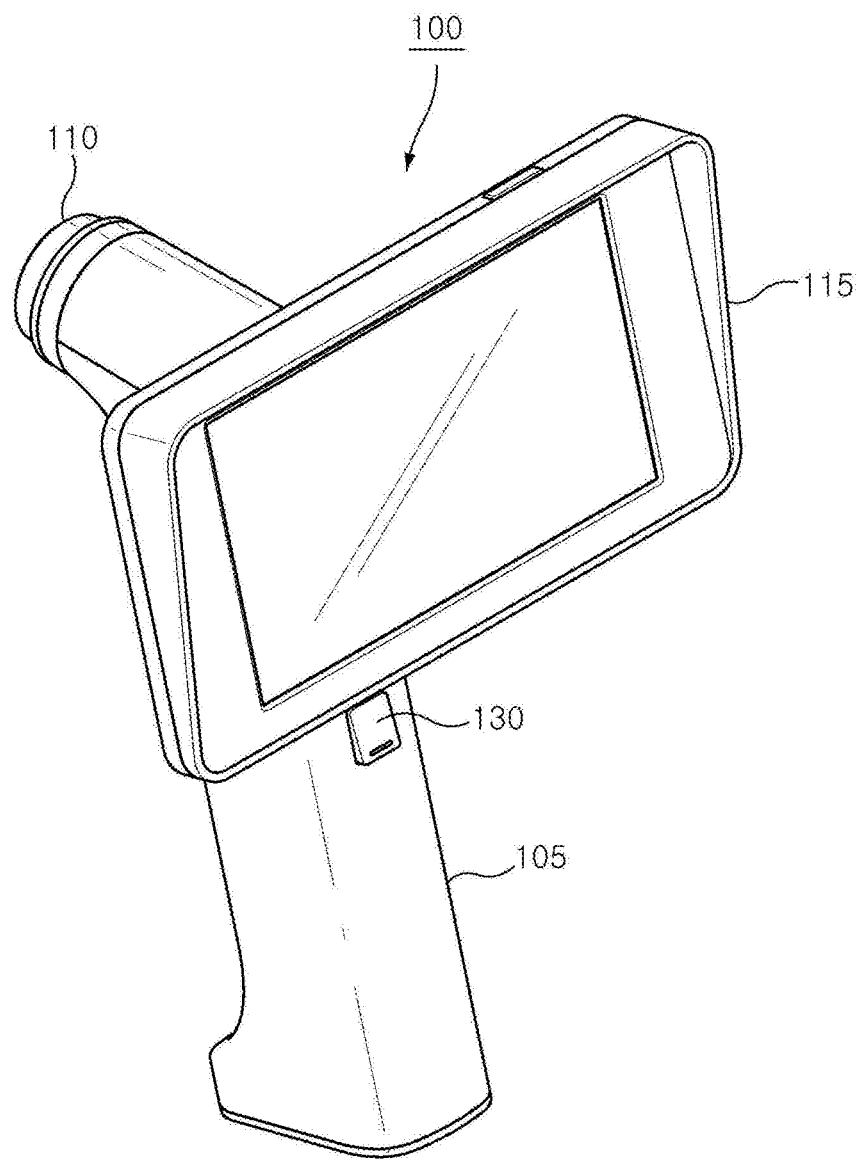
FIG. 1 is an exemplary view of an exterior of a main body (100) of a uterine cervical image acquisition apparatus according to an embodiment of the present invention.
Figure 2:
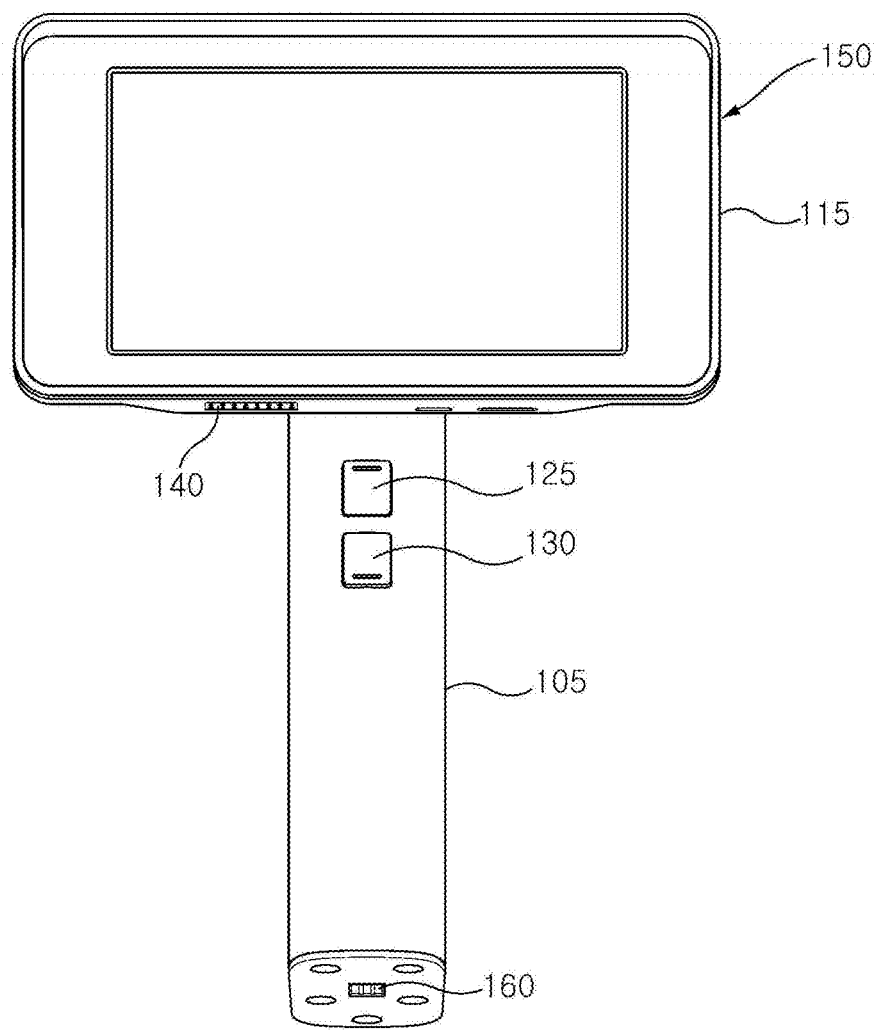
FIG. 2 is an exemplary rear view of the main body (100) of the uterine cervical image acquisition apparatus of FIG. 1.
Figure 3:
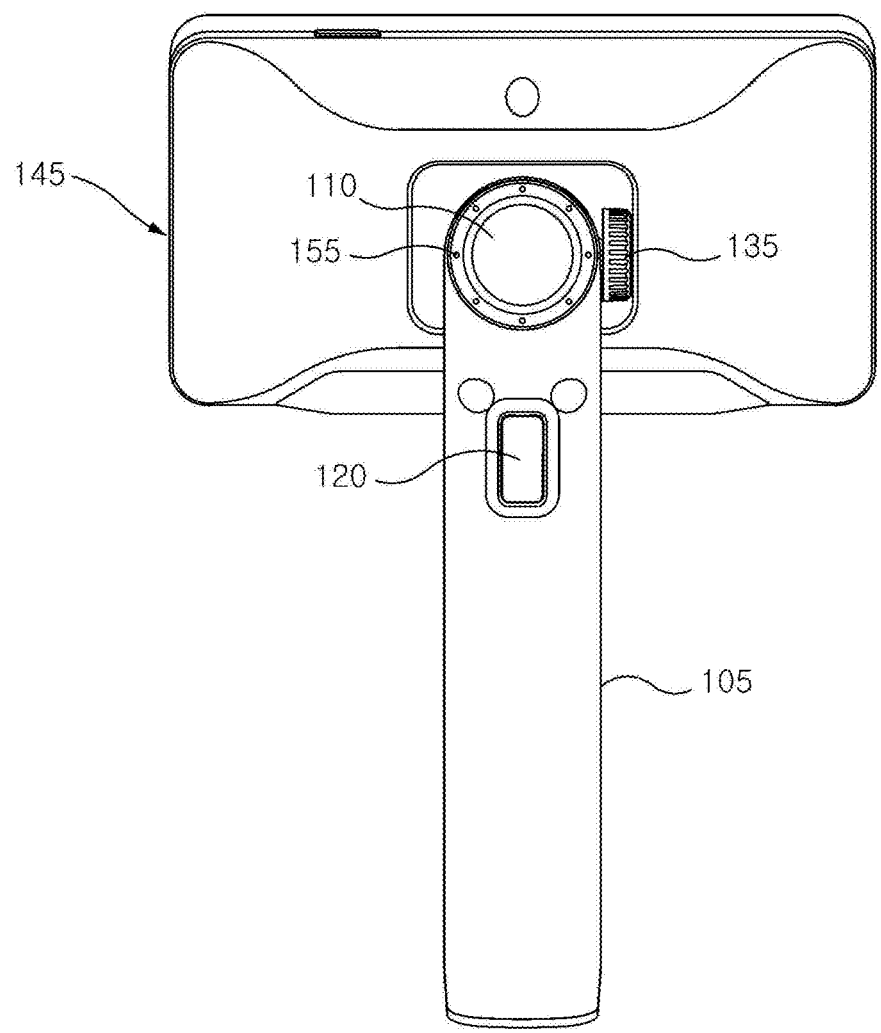
FIG. 3 is an exemplary front view of the main body (100) of the uterine cervical image acquisition apparatus of FIG. 1.
Figure 4:
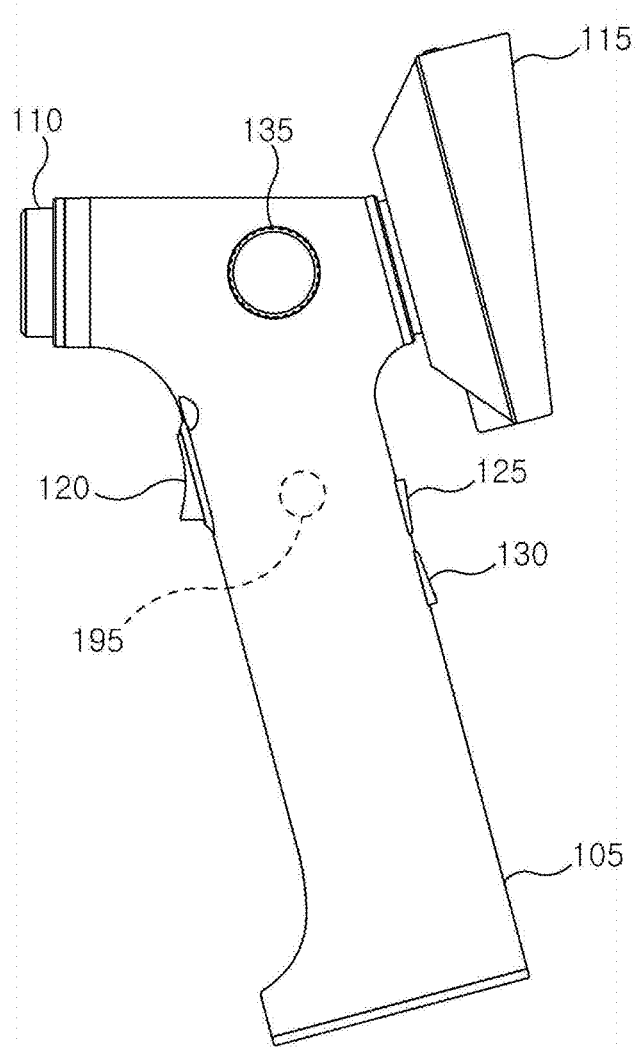
FIG. 4 is an exemplary side view of the main body (100) of the uterine cervical image acquisition apparatus of FIG. 1.

First, FIG. 1 is an exemplary view of an exterior of a main body 100 of a uterine cervical image acquisition apparatus according to an embodiment of the present invention, FIG. 2 is an exemplary rear view of the main body 100 of the uterine cervical image acquisition apparatus of FIG. 1, FIG. 3 is an exemplary front view of the main body 100 of the uterine cervical image acquisition apparatus of FIG. 1, and FIG. 4 is an exemplary side view of the main body 100 of the uterine cervical image acquisition apparatus of FIG. 1.

As illustrated in FIGS. 1 to 4, the uterine cervical image acquisition apparatus according to the embodiment of the present invention includes a main body 100 in which a camera 110 having an auto-focusing function for acquiring a uterine cervical image is installed on one side (the front) thereof, a user interface 115 for displaying the uterine cervical image and inputting a user touch command is installed on a side (the rear) opposite to the one side, and a handlebar unit 105 is formed to protrude in a downward direction.

As illustrated in FIG. 3, a light source unit 155 that irradiates a front of the main body 100 with light in a forward direction is disposed around a lens unit constituting the camera 110. The illuminance of the light source unit 155 is adjusted by operating a brightness control dial 135 illustrated in FIG. 4.

For reference, the user interface 115 may be implemented using a touch screen to display a captured uterine cervical image and input a user command. As illustrated in FIG. 4, an upper end of a display surface of the touch screen is further inclined in a direction (forward direction) in which the camera 110 is installed as compared to a lower end thereof, and thus, in photographing a uterine cervix of a patient to be treated who lying down, a medical practitioner may comfortably photograph the uterine cervix without bending or lowering any part of her body. In the embodiment of the present invention, although the user interface 115 is illustrated as being fixed to be inclined, the user interface 115 may be mechanically designed to be movable in lateral and vertical directions.

Furthermore, as illustrated in FIGS. 2 and 3, a power button 150 and a secure digital (SD) card insertion slot 145 are formed at one side surface of the user interface 115, and a speaker 140 is formed on a lower surface of the user interface 115, and thus the above components are designed so that the captured uterine cervical image to be stored is supported and recorded sound is reproduced and output.

Meanwhile, the handlebar unit 105 protrudes downward from the main body 100, which extends by a predetermined length in a horizontal direction, wherein a battery (not illustrated) for supplying power for charging and operation is built-in inside the handlebar unit 105, and a charging terminal 160 for supplying power for charging the built-in battery by being electrically connected to a charging unit (or a charging pin) formed in a charging stand 200 to be described below is formed on a bottom surface of the handlebar unit 105. In addition, as illustrated in FIGS. 1 to 4, a plurality of operation buttons are formed on the handlebar unit 105 for user convenience when photographing, wherein an image capturing button 120 operated by an index finger is formed in a front of the handlebar unit 105, and a zoom-in button 125 and a zoom-out button 130 operated by a thumb are formed in the rear of the handlebar unit 105 to provide convenience of operation when photographing.

Figure 5:
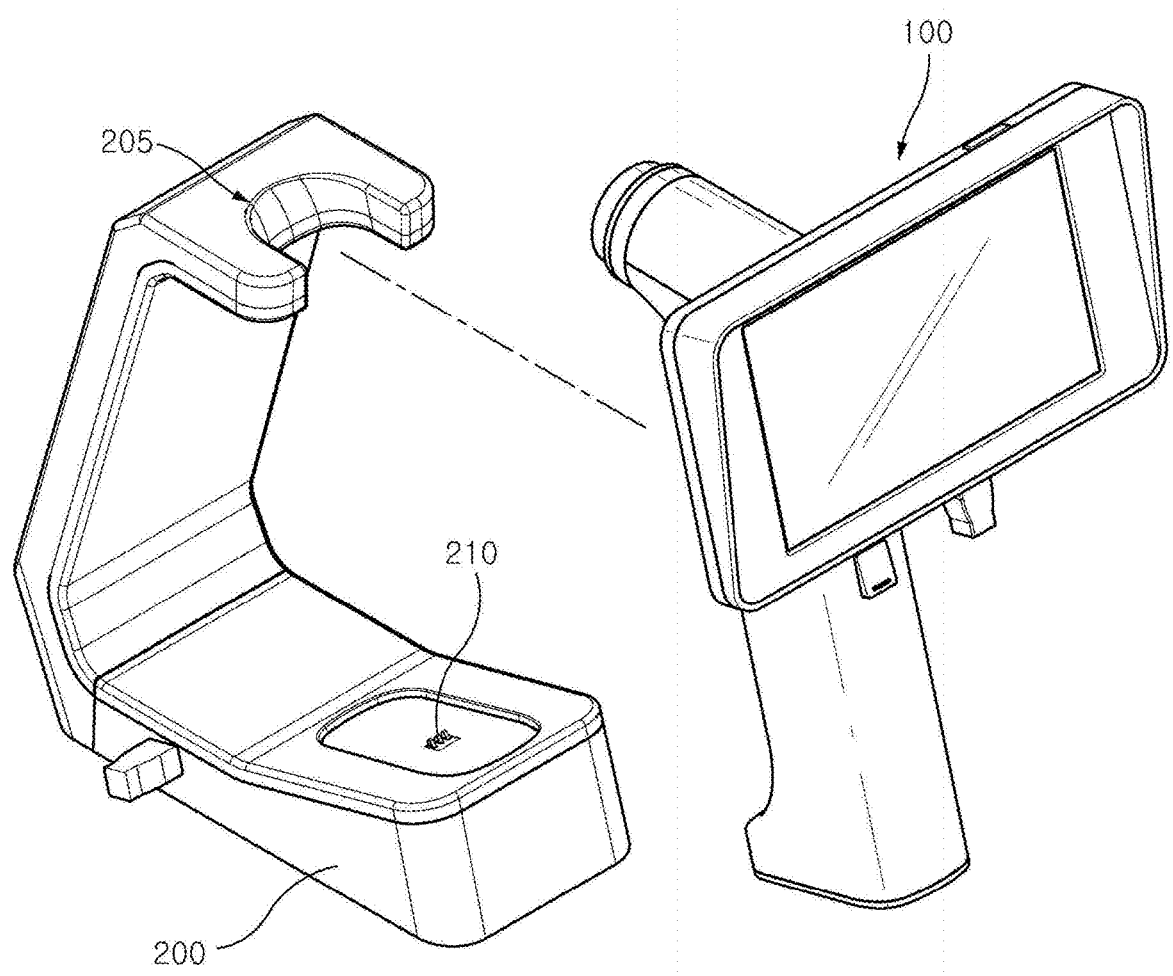
FIG. 5 is an exemplary view of an exterior of a uterine cervical image acquisition apparatus including a charging stand (200) according to an embodiment of the present invention.

The main body 100 of the uterine cervical image acquisition apparatus having the mechanical configuration and structural features described above may be configured as a single uterine cervical image acquisition apparatus, and in some cases, the charging stand 200 and the main body 100 of the uterine cervical image acquisition apparatus may be configured as a single uterine cervical image acquisition apparatus, as illustrated in FIG. 5.

FIG. 5 is an exemplary view of an exterior of a uterine cervical image acquisition apparatus including a charging stand 200 according to another embodiment of the present invention. The uterine cervical image acquisition apparatus according to another embodiment of the present invention may include the main body 100 described in FIGS. 1 to 4 and may further include the charging stand 200 in which a charging unit 210 to be connected to the charging terminal 160 formed on a lower end of a bottom surface of the handlebar unit 105 of the main body 100 is formed and a coupling groove 205, which an upper end of the handlebar unit 105 is coupled to and supported in, is formed. Hereinafter, the electronic configuration of the uterine cervical image acquisition apparatus having the above-described mechanical configuration and structural features will be described in detail.

Figure 6:
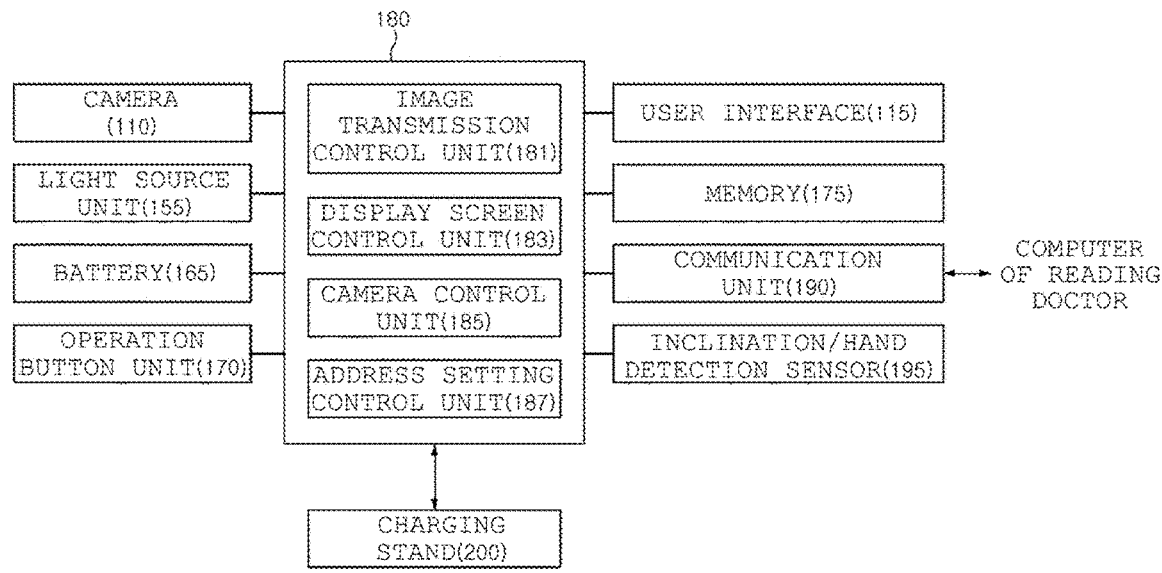
FIG. 6 is an exemplary block diagram of a uterine cervical image acquisition apparatus according to an embodiment of the present invention.
Figure 7:
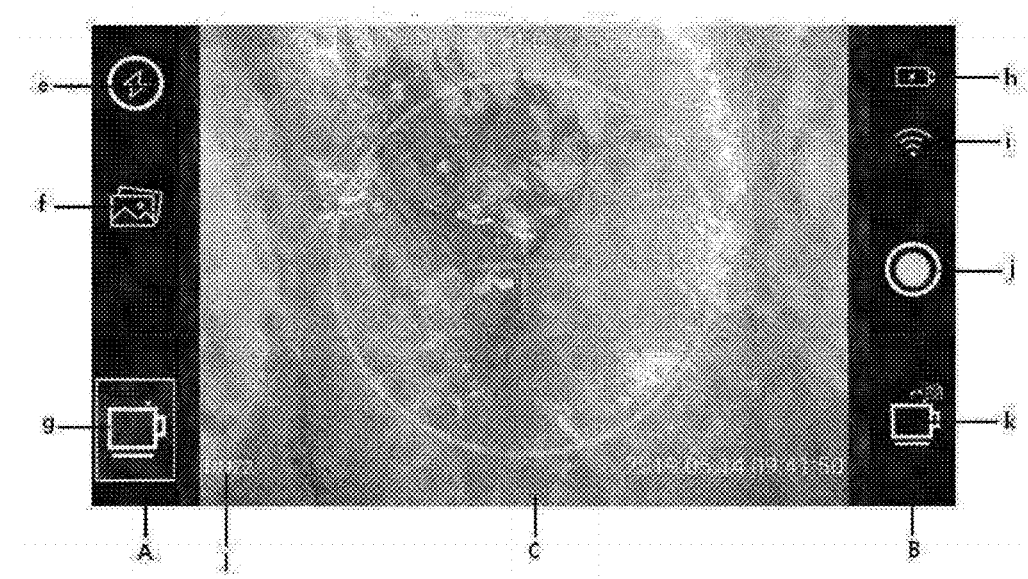
FIG. 7 is an exemplary view of display positions of menu bars (A and B) displayed on a user interface of a main body (100) of a uterine cervical image acquisition apparatus according to an embodiment of the present invention.

First, FIG. 6 is an exemplary block diagram of a main body 100 of a uterine cervical image acquisition apparatus according to an embodiment of the present invention, and FIG. 7 is an exemplary view of display positions of menu bars A and B displayed on a user interface 115 of the main body 100 of the uterine cervical image acquisition apparatus according to the embodiment of the present invention.

The uterine cervical image acquisition apparatus according to the embodiment of the present invention includes a memory 175 for storing the captured uterine cervical image, a short-range communication unit (Wi-Fi module and/or Bluetooth module) 190 for transmitting the uterine cervical image to a computer of a reading doctor, and a control unit 180 for controlling the overall operation of the uterine cervical image acquisition apparatus in addition to the camera 110, the user interface 115, the light source unit 155, the battery 165, and an operation button unit 170 which includes the image capturing button, the zoom-in button, the zoom-out button, and the plurality of buttons which are described above.

More specifically, the control unit 180 includes an image transmission control unit 181 for performing control to store captured uterine cervical images in the memory 175, encrypt a uterine cervical image selected by a user of the apparatus, and transmit the encrypted uterine cervical image to the computer of the reading doctor, a display screen control unit 183 for performing control to display the captured uterine cervical image and menu bars for receiving user touch commands on left and right or upper and lower sides of the captured uterine cervical image, and a camera control unit 185 for controlling zooming and auto-focusing of the camera 110 and brightness (illuminance) of the light source unit 155 according to operations of the provided button.

According to the implementation method, the control unit 180 may further include an address setting control unit 187 for automatically setting an Internet protocol (IP) address/port number of the computer of the reading doctor using a quick response (QR) code obtained through the camera 110. The QR code is information generated by an application program installed on the computer of the reading doctor, and includes the information on the IP address and port number of the computer of the reading doctor. Additionally, as illustrated in FIG. 7, the display screen control unit 183 may display the menu bars A and B, which are displayed on left and right (or up and down) sides of a captured uterine cervical image D, on any one menu bar or may change and display (i.e., change display positions of function buttons displayed on the menu bars) the display positions of the menu bars A and B in opposite directions whenever a left and right hand mode setting button displayed when the setting button is pressed is operated. This is for providing convenience of operation of the function buttons displayed on the menu bars in consideration of a left-handed person or a right-handed person.

Furthermore, as illustrated in FIG. 7, the display screen control unit 183 may display a green filter on/off button on the menu bar B, and may apply and process a green filter to the uterine cervical image when a green filter on is selected.

Meanwhile, since the above-described left and right hand mode setting is manually performed, the left and right hand mode may be set to be automatically performed for user convenience. To this end, as illustrated in FIG. 4, when a hand detection sensor 195 for detecting a left hand or right hand holding the handlebar unit 105 is formed on the handlebar unit 105 constituting the main body 100 of the uterine cervical image acquisition apparatus to be exposed, the display screen control unit 183 may detect the user's hand holding the handlebar unit 105 through the hand detection sensor 195 and automatically change and display the positions of the menu bars A and B. As the hand detection sensor 195, an optical sensor that responds to a change in illuminance may be used, and a proximity sensor or a heat sensor that detects and responds to a hand approaching may be used.

Furthermore, as another modified embodiment, the uterine cervical image acquisition apparatus may further include an inclination sensor for detecting a degree of inclination of the main body 100 (or the handlebar unit 105) with respect to the ground. When the display screen control unit 183 corrects inclination of the captured uterine cervical image according to a value of the inclination obtained by the inclination sensor, the inclination of the uterine cervical image may be corrected according to the value of the inclination even when the uterine cervix is photographed in a state in which the uterine cervical image acquisition apparatus is inclined. Therefore, it is possible to obtain the same effect as photographing the uterine cervix in a state in which the main body 100 of the uterine cervical image acquisition apparatus is positioned in a fixed position without inclination with respect to the ground. Therefore, the medical practitioner photographing the uterine cervix may photograph the uterine cervix while holding the handlebar unit 105 of the uterine cervical image acquisition apparatus most comfortably.

Meanwhile, the uterine cervical image acquisition apparatus according to another embodiment of the present invention may further include a charging stand 200 in which a charging unit 210 to be connected to a charging terminal 160 formed on a lower end of a bottom surface of the handlebar unit 105 is formed and a coupling groove 205, which an upper end of the handlebar unit 105 is coupled to and supported in, is formed.

In addition to the technical components described above, the uterine cervical image acquisition apparatus according to another embodiment of the present invention, along with a collection of pieces of data of an application program for a reading doctor, may constitute a uterine cervical image acquisition apparatus, wherein the application program is installed and executed in a memory of the computer of the reading doctor to decrypt the uterine cervical image encrypted and transmitted by the main body 100 of the uterine cervical image acquisition apparatus and display the decrypted uterine cervical image on a display unit.

The collection of the pieces of data of the application program for a reading doctor may include a machine learning model for uterine cervical cancer, which learns the characteristics of learning data required for automatic diagnosis of the uterine cervical cancer, and a uterine cervical cancer diagnosis model, which generates and displays diagnostic information on the onset of uterine cervical cancer with respect to the decrypted uterine cervical image on the basis of the machine learning model.

Furthermore, the uterine cervical cancer diagnosis model generates the diagnostic information on the onset of the uterine cervical cancer according to one or more diagnostic criteria selected by the reading doctor from among a color, a size of a uterine cervix in the uterine cervical image, and a malignant atypical blood vessel pattern.

For reference, in an acetic acid reaction image, because a white stain appears on the uterine cervix, the uterine cervix may be distinguished from a pink uterine cervix and vagina. Since a Lugol's solution reaction image shows brown or dark orange color, and a green filter image shows strong green throughout the image, it is possible to diagnose the onset of uterine cervical cancer using the color value representing the characteristics of each image.

Figure 8:
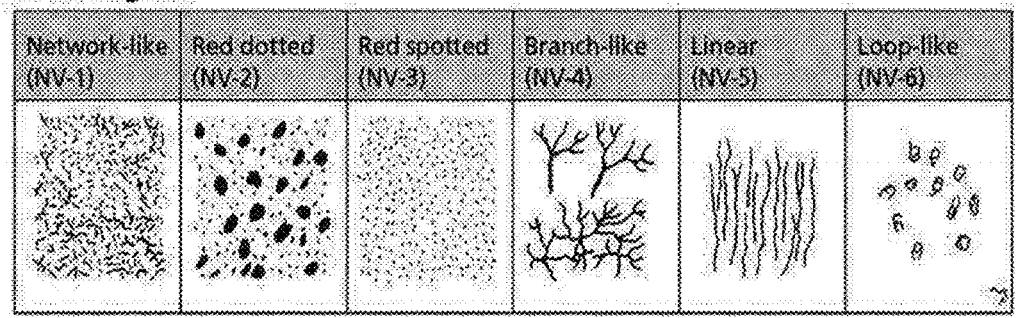
FIG. 8 illustrates exemplary views of malignant atypical blood vessels.
Figure 8:
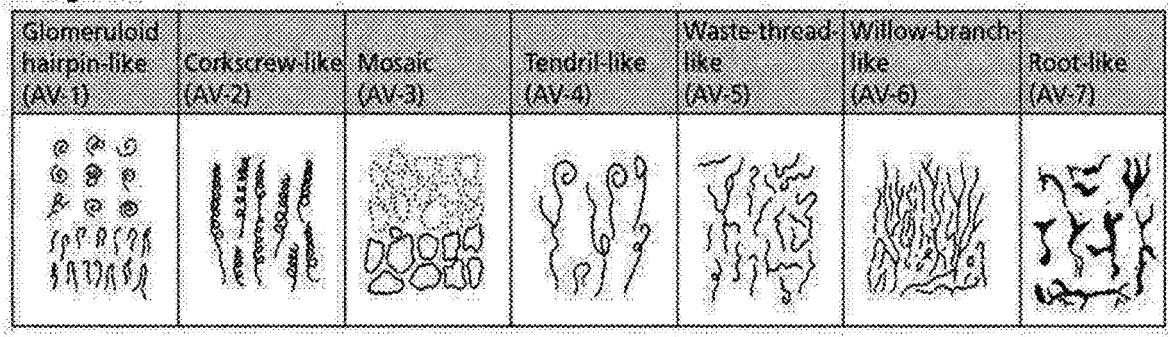

FIG. 8 illustrates exemplary views of malignant atypical blood vessels. When training of the malignant atypical blood vessel patterns illustrated in FIG. 8 is performed, the uterine cervical cancer diagnosis model may generate a diagnosis of the onset of a uterine cervical cancer showing a malignant atypical blood vessel pattern on the basis of the trained machine learning model.

The above-described machine learning model and uterine cervical cancer diagnosis model may be installed on a diagnosis server located at a remote location in the form of application programs for diagnosing uterine cervical cancer, and may also be installed and operated on the computer of the reading doctor.

Hereinafter, the operation of the uterine cervical image acquisition apparatus having the above-described mechanical and electronic configuration will be described in more detail with reference to the accompanying drawings.

Figure 9:
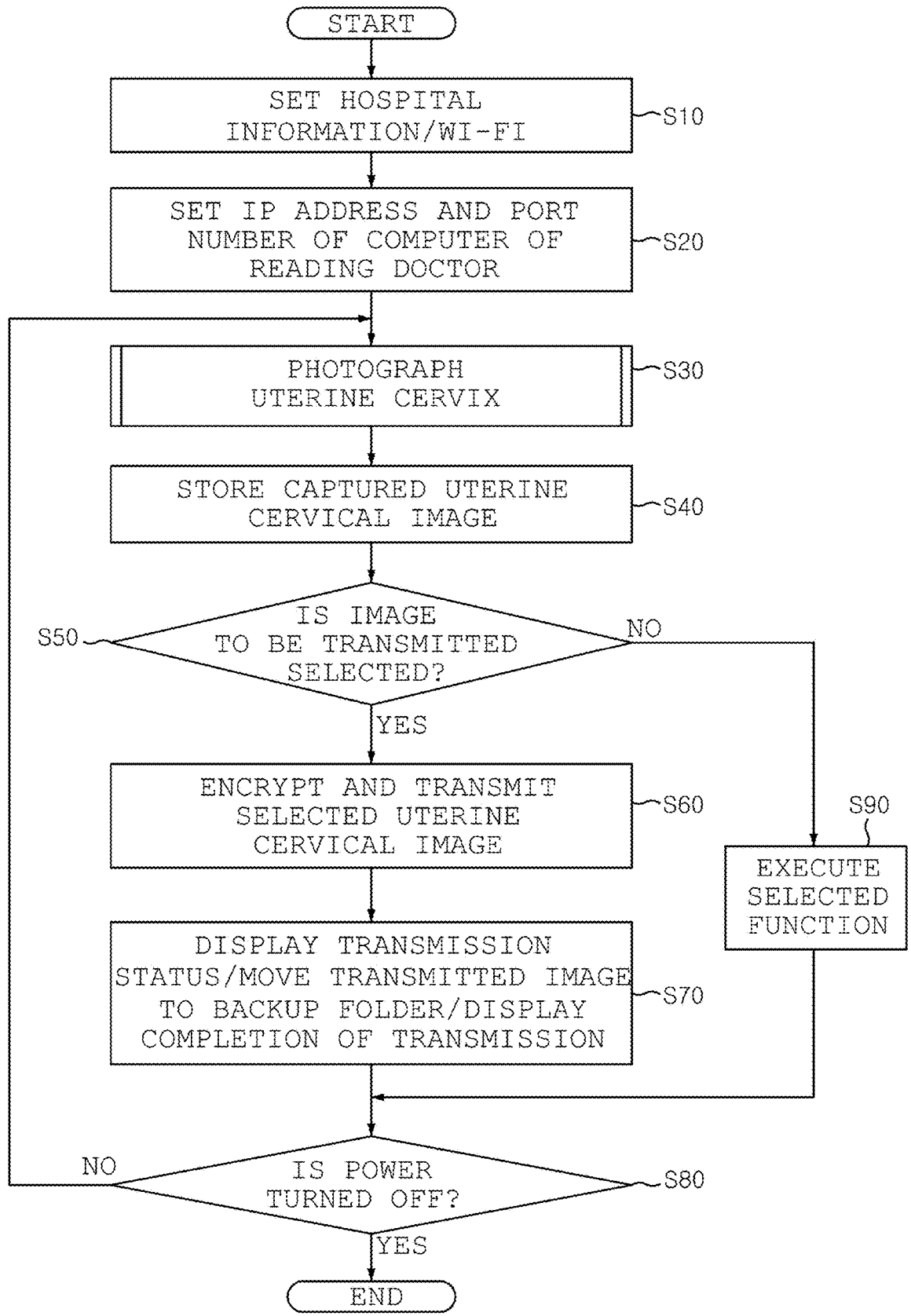
FIG. 9 is a flowchart illustrating operations of a uterine cervical image acquisition apparatus according to an embodiment of the present invention.
Figure 10:
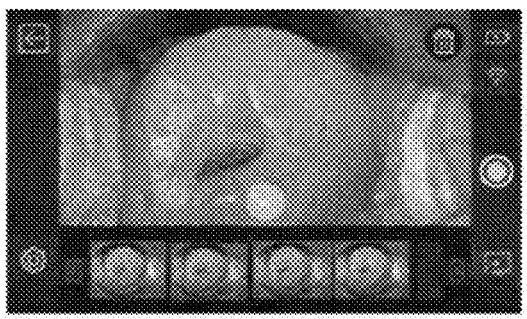
FIG. 10 illustrates exemplary views of a display screen of a uterine cervical image acquisition apparatus according to an embodiment of the present invention.
Figure 10:
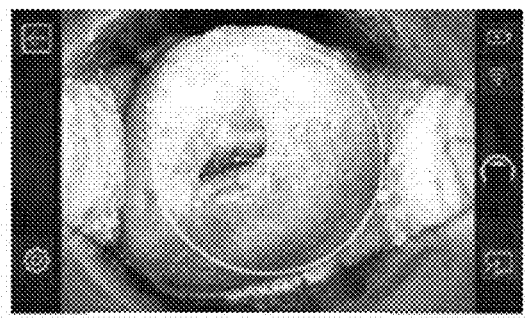
Figure 10:
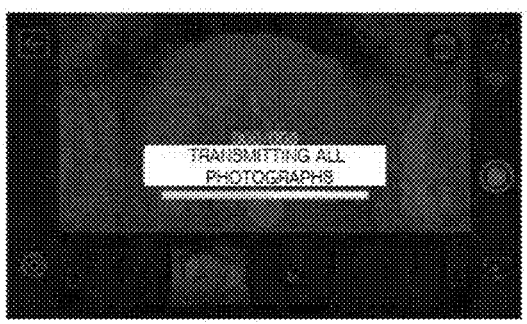
Figure 10:
Figure 11:
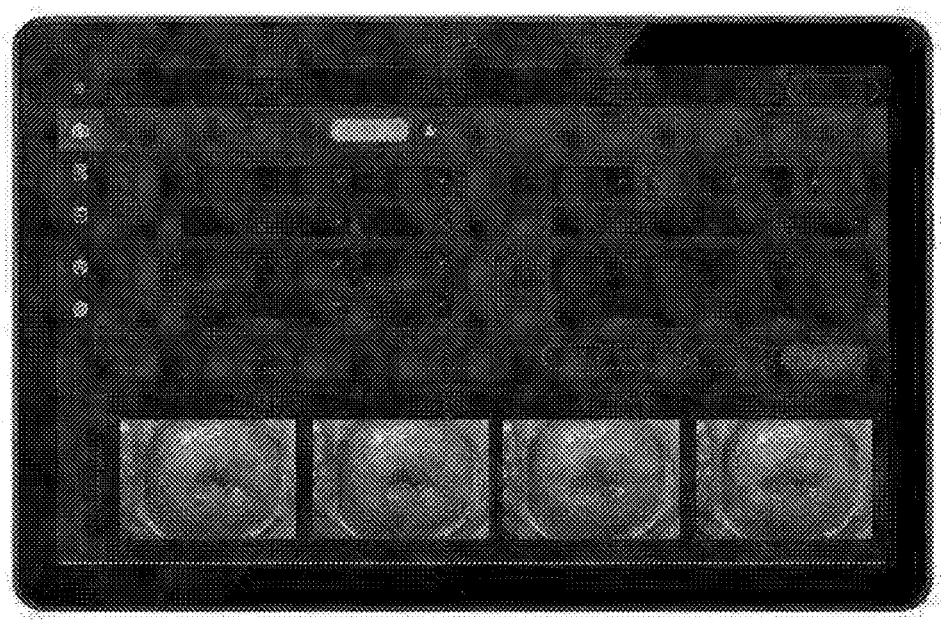
FIG. 11 is an exemplary view of a reading request screen displayed on a computer of a reading doctor according to an embodiment of the present invention.

FIG. 9 is a flowchart illustrating operations of a uterine cervical image acquisition apparatus according to an embodiment of the present invention, FIG. 10 illustrates exemplary views of a display screen of the uterine cervical image acquisition apparatus according to the embodiment of the present invention, and FIG. 11 is an exemplary view of a reading request screen displayed on a computer of a reading doctor according to the embodiment of the present invention.

Referring to FIG. 9, first, when power is turned on by operating a power button 150 provided on the uterine cervical image acquisition apparatus, a display screen control unit 183 displays a screen for setting a hospital name on a user interface 115 as a first execution screen. Accordingly, a user of the apparatus sets the hospital name. When the setting of the hospital name is completed, the display screen control unit 183 displays a screen for setting Wi-Fi (Bluetooth) on a user interface 115 so that the user of the apparatus sets connectable Wi-Fi (S10).

Then, the display screen control unit 183 displays a screen for setting an IP address and port number of the computer of the reading doctor on the user interface 115. The display screen may include an information input box, in which the user of the apparatus can directly input information on the IP address and port number of the computer of the reading doctor, and include a button instructing to scan a QR code provided by an application program for a reading doctor which is installed in the computer of the reading doctor in order to provide convenience of inputting information.

For reference, the user of the apparatus installs an application program necessary for decrypting the uterine cervical image, which is captured by the uterine cervical image acquisition apparatus and transmitted, and displaying the decrypted uterine cervical image on the display unit, that is, the application program for a reading doctor, in a memory of the computer of the reading doctor. The user of the apparatus may execute the application program for a reading doctor installed on the computer of the reading doctor to input and set pieces of information necessary for normal information transmission/reception between the uterine cervical image acquisition apparatus and the computer of the reading doctor.

Above all, the application program for a reading doctor accesses the information on the IP address and port number set in the computer of the reading doctor, converts the information on the IP address and port number into a QR code, and displays the QR code on the screen. Accordingly, when the user of the apparatus scans the QR code displayed on the computer of the reading doctor using a camera 110 provided in the uterine cervical image acquisition apparatus, an address setting control unit 187 reads the QR code obtained using the camera 110 and automatically sets the information on the IP address and port number of the computer of the reading doctor (S20).

When the settings of the IP address and port number are completed, the display screen control unit 183 may display a screen for sequentially setting a date and a password on the user interface 115 so that the user of the apparatus may input or set various pieces of information necessary for using the apparatus.

When the above-described information inputting or setting is completed, the user of the apparatus may capture a uterine cervix or record a video using function buttons g and k provided on menu bars A and B displayed on the left and right of a region C on which a camera image is displayed, as illustrated in FIG. 7 (S30). In FIG. 7, "I" indicates a hospital name, "e" indicates a flash on/off button, "f" indicates an album move button, "g" indicates a capture/video recording button, "k" indicates a capture/video change button, "h" indicates a battery status, "I" indicates a Wi-Fi connection status, and "j" indicates a green filter on/off button. The function buttons provided on the menu bars A and B are only examples, and a (system) setting button and a left and right hand mode setting (or change) button may be further provided on the menu bar A or B. Positions of the menu bars A and B are changed from left to right and from right to left whenever the left and right hand mode setting buttons are operated. The left and right hand mode may be set in a (system) setting mode without a display button. In some cases, as illustrated in FIG. 5, the hand detection sensor 195 may be provided to detect a hand holding the handlebar unit 105, and the display positions of the menu bars A and B may be changed.

Hereinafter, the process of capturing the uterine cervix and transmitting the image of the uterine cervix will be described in detail. The user of the apparatus photographs a uterine cervix of a patient to be treated while holding the handlebar unit 105 of the main body 100 of the uterine cervical image acquisition apparatus with her left or right hand.

In this case, when the brightness of the uterine cervix appearing on the display screen is dark, the illuminance of a light source unit 155 is adjusted using a brightness control dial 135.

After a position of the main body 100 of the uterine cervical image acquisition apparatus is adjusted so that, after the brightness is adjusted, the uterine cervix is placed at the center of the display screen, when the image capturing button 120 starts to be pressed, auto-focusing on the uterine cervix is performed, and when the image capturing button 120 is pressed again after the auto-focusing is completed, the uterine cervix appearing on the display screen is photographed (S30). The uterine cervical image captured in this way is stored in a memory 175 (S40). Examples of the sequentially photographed and stored album and a "Picture album" screen are illustrated in FIG. 10.

The user of the apparatus may photograph a plurality of captured screens for the uterine cervix as necessary, and then select a necessary uterine cervix captured screen from the album and transmit the necessary uterine cervix captured screen to the computer of the reading doctor. That is, when the selection of the image to be transmitted by the user of the apparatus is completed (S50), the image transmission control unit 181 encrypts the selected uterine cervical image and transmits the encrypted uterine cervical image to the computer of the reading doctor having the information on the IP address and port number set through the communication unit 190 (S60).

When the uterine cervical image is transmitted, a transmission status is displayed as illustrated in a "Wireless transfer" screen of FIG. 10, and when the transmission is completed, the transmitted image is moved and stored in a backup folder, and the fact that the transmission to the user of the apparatus is completed is displayed in a pop-up manner (S60). For reference, a "Green filter" screen of FIG. 10 is an example of a screen obtained by photographing the uterine cervix by applying (turning on) a green filter.

When the uterine cervical image which is captured and encrypted by the uterine cervical image acquisition apparatus is transmitted to the computer of the reading doctor, the application program installed on the computer of the reading doctor decrypts the encrypted and transmitted uterine cervical image, stores the decrypted uterine cervical image in a storage device, and at the same time, displays the decrypted uterine cervical image on the reading request screen illustrated in FIG. 11. Accordingly, the reading doctor selects the uterine cervical image displayed on the reading request screen and determines whether there is an abnormality.

When the application program for a reading doctor is an application program including a machine learning model which learns the characteristics of learning data for uterine cervical cancer and a uterine cervical cancer diagnosis model which generates and displays diagnostic information on the onset of uterine cervical cancer on the basis of the machine learning model, it is possible to automatically diagnose the onset of uterine cervical cancer in the encrypted and transmitted uterine cervical image on the basis of the machine learning model and display a result of the automatic diagnosis on a part of the reading request screen.

In this case, in order to verify the result of the automatic diagnosis for the uterine cervical cancer, the reading doctor re-reads the uterine cervical image, and when the result of the automatic diagnosis is incorrect, the reading doctor checks a cause of the misdiagnosis and corrects the cause. Evaluation information by the reading doctor is transmitted to a designated management server through a network according to an evaluation information transmission command of the reading doctor, and may be utilized for re-learning of the machine learning model.

As described above, in the uterine cervical image acquisition apparatus according to the embodiment of the present invention, it is possible to capture the uterine cervical image using the camera 110 and wirelessly transmit the captured image to the designated computer of the reading doctor according to a command of the user of the apparatus, and thus the inconvenience of connection of the uterine cervical image acquisition apparatus and the computer of the reading doctor using a cable can be eliminated.

Furthermore, an upper portion of the user interface 115 installed in the rear of the uterine cervical image acquisition apparatus is inclined in a forward direction, and thus, in photographing the uterine cervix of a patient to be treated who lying down, the user of the apparatus has a convenience of being able to photograph the uterine cervix while viewing the photographing screen conveniently without bending any part of her body such as a knee or head.

Further, a camera image is displayed on the user interface 115 of the uterine cervical image acquisition apparatus according to the embodiment of the present invention and menu bars A and B, in which a plurality of function buttons for apparatus operation and settings are displayed, are all displayed on left and right or upper and lower sides of a region in which the camera image is displayed, and thus there is an advantage in that it can be conveniently operated by holding the handlebar unit 105 with one hand and inputting a touch input on the function buttons provided on the menu bars A and B with the other hand.

Further, in the uterine cervical image acquisition apparatus according to the embodiment of the present invention, main function buttons that are frequently used are positioned to be focused on one of the menu bars A and B, and the position of the menu bar is manually or automatically changed and displayed for a left-handed person or a right-handed person, and thus an effect of providing convenience in operating the apparatus may be obtained.

When the uterine cervical image acquisition apparatus according to the embodiment of the present invention is a uterine cervical image acquisition apparatus capable of correcting the inclination of the captured display image by detecting the inclination of the main body 100, there is an advantage in that a uterine cervical image positioned at a correct position may be acquired even when the uterine cervix is photographed in a state in which the main body 100 is inclined.

Further, in the present invention, there is a convenience of being able to conveniently set the information on the IP address and port number of the computer of the reading doctor only by scanning the QR code displayed under the support of the application program installed on the computer of the reading doctor.

While the invention has been described with reference to specific details such as detailed components, specific embodiments, and drawings, these are only examples to facilitate overall understanding of the invention and the invention is not limited thereto. It will be understood by those skilled in the art that various modifications and alterations may be made.

Therefore, the spirit and scope of the present invention are defined not by the detailed description of the present invention but by the appended claims, and encompasses all modifications and equivalents that fall within the scope of the appended claims.

What is claimed is:

1. A uterine cervical image acquisition apparatus including a main body in which a camera for acquiring a uterine cervical image is installed on one side thereof, a user interface for displaying the uterine cervical image and inputting a user touch command is installed on a side opposite to the one side, and a handlebar unit is formed in a downward direction, a light source unit that irradiates a front of the main body with light, a battery which is positioned in the handlebar unit to supply power for charging and operation, and an operation button unit which at least includes an image capturing button, a zoom-in button, and a zoom-out button formed on the handlebar unit, the uterine cervical image acquisition apparatus comprising:
   a memory configured to store the captured uterine cervical image;
   a communication unit configured to transmit the uterine cervical image to a computer of a reading doctor;
   an image transmission control unit configured to perform control to store the captured uterine cervical image in the memory, encrypt the selected uterine cervical image, and transmit the encrypted uterine cervical image to the computer of the reading doctor;
   a display screen control unit configured to perform control to display the captured uterine cervical image and menu bars for receiving the user touch command on left and right or upper and lower sides of the captured uterine cervical image; and
   a camera control unit configured to control zooming and auto-focusing of the camera and brightness of the light source unit according to operations of the provided button.

2. The uterine cervical image acquisition apparatus of claim 1, wherein the display screen control unit changes display positions of the menu bars in opposite directions and displays the menu bars whenever a left and right hand mode setting button displayed on the menu bar is operated.

3. The uterine cervical image acquisition apparatus of claim 1, further comprising an inclination sensor configured to detect a degree of inclination of the main body,
   wherein the display screen control unit corrects inclination of the captured uterine cervical image according to the inclination detected by the inclination sensor.

4. The uterine cervical image acquisition apparatus of claim 1, further comprising a charging stand in which a charging unit to be connected to a charging terminal formed on a lower end of a bottom surface of the handlebar unit is formed, and a coupling groove, which an upper end of the handlebar unit is coupled to and supported in, is formed.

5. The uterine cervical image acquisition apparatus of claim 1, further comprising a collection of pieces of data of an application program for a reading doctor, wherein the application program is installed and executed in a memory of the computer of the reading doctor to decrypt the encrypted and transmitted uterine cervical image and display the decrypted uterine cervical image.

6. The uterine cervical image acquisition apparatus of claim 5, wherein the collection of the pieces of data of the application program for a reading doctor includes a machine learning model for uterine cervical cancer, which learns characteristics of learning data, and a uterine cervical cancer diagnosis model, which generates and displays diagnostic information on the onset of uterine cervical cancer with respect to the decrypted uterine cervical image on the basis of the machine learning model.

7. The uterine cervical image acquisition apparatus of claim 6, wherein the uterine cervical cancer diagnosis model generates the diagnostic information on the onset of the uterine cervical cancer according to one or more diagnostic criteria selected by the reading doctor from among a color, a size of a uterine cervix in the uterine cervical image, and a malignant atypical blood vessel pattern.

8. The uterine cervical image acquisition apparatus of claim 1, wherein the display screen control unit displays a green filter on/off button on the menu bar and applies and processes a green filter to the uterine cervical image when a green filter on is selected.

9. The uterine cervical image acquisition apparatus of claim 1, wherein an upper end of a display surface of the user interface is further inclined in a direction in which the camera is installed as compared to a lower end thereof.

10. The uterine cervical image acquisition apparatus of claim 2, further comprising a collection of pieces of data of an application program for a reading doctor, wherein the application program is installed and executed in a memory of the computer of the reading doctor to decrypt the encrypted and transmitted uterine cervical image and display the decrypted uterine cervical image.

11. The uterine cervical image acquisition apparatus of claim 3, further comprising a collection of pieces of data of an application program for a reading doctor, wherein the application program is installed and executed in a memory of the computer of the reading doctor to decrypt the encrypted and transmitted uterine cervical image and display the decrypted uterine cervical image.

12. The uterine cervical image acquisition apparatus of claim 4, further comprising a collection of pieces of data of an application program for a reading doctor, wherein the application program is installed and executed in a memory of the computer of the reading doctor to decrypt the encrypted and transmitted uterine cervical image and display the decrypted uterine cervical image.

13. The uterine cervical image acquisition apparatus of claim 2, wherein the display screen control unit displays a green filter on/off button on the menu bar and applies and processes a green filter to the uterine cervical image when a green filter on is selected.

14. The uterine cervical image acquisition apparatus of claim 3, wherein the display screen control unit displays a green filter on/off button on the menu bar and applies and processes a green filter to the uterine cervical image when a green filter on is selected.

15. The uterine cervical image acquisition apparatus of claim 4, wherein the display screen control unit displays a green filter on/off button on the menu bar and applies and processes a green filter to the uterine cervical image when a green filter on is selected.

16. The uterine cervical image acquisition apparatus of claim 2, wherein an upper end of a display surface of the user interface is further inclined in a direction in which the camera is installed as compared to a lower end thereof.

17. The uterine cervical image acquisition apparatus of claim 3, wherein an upper end of a display surface of the user interface is further inclined in a direction in which the camera is installed as compared to a lower end thereof.

18. The uterine cervical image acquisition apparatus of claim 4, wherein an upper end of a display surface of the user interface is further inclined in a direction in which the camera is installed as compared to a lower end thereof.

19. The uterine cervical image acquisition apparatus of claim 10, wherein the collection of the pieces of data of the application program for a reading doctor includes a machine learning model for uterine cervical cancer, which learns characteristics of learning data, and a uterine cervical cancer diagnosis model, which generates and displays diagnostic information on the onset of uterine cervical cancer with respect to the decrypted uterine cervical image on the basis of the machine learning model.

20. The uterine cervical image acquisition apparatus of claim 11, wherein the collection of the pieces of data of the application program for a reading doctor includes a machine learning model for uterine cervical cancer, which learns characteristics of learning data, and a uterine cervical cancer diagnosis model, which generates and displays diagnostic information on the onset of uterine cervical cancer with respect to the decrypted uterine cervical image on the basis of the machine learning model.

21. The uterine cervical image acquisition apparatus of claim 12, wherein the collection of the pieces of data of the application program for a reading doctor includes a machine learning model for uterine cervical cancer, which learns characteristics of learning data, and a uterine cervical cancer diagnosis model, which generates and displays diagnostic information on the onset of uterine cervical cancer with respect to the decrypted uterine cervical image on the basis of the machine learning model.

22. The uterine cervical image acquisition apparatus of claim 19, wherein the uterine cervical cancer diagnosis model generates the diagnostic information on the onset of the uterine cervical cancer according to one or more diagnostic criteria selected by the reading doctor from among a color, a size of a uterine cervix in the uterine cervical image, and a malignant atypical blood vessel pattern.

23. The uterine cervical image acquisition apparatus of claim 20, wherein the uterine cervical cancer diagnosis model generates the diagnostic information on the onset of the uterine cervical cancer according to one or more diagnostic criteria selected by the reading doctor from among a color, a size of a uterine cervix in the uterine cervical image, and a malignant atypical blood vessel pattern.

24. The uterine cervical image acquisition apparatus of claim 21, wherein the uterine cervical cancer diagnosis model generates the diagnostic information on the onset of the uterine cervical cancer according to one or more diagnostic criteria selected by the reading doctor from among a color, a size of a uterine cervix in the uterine cervical image, and a malignant atypical blood vessel pattern.

* * * * *